US007674867B2

(12) United States Patent
Ijpeij et al.

(10) Patent No.: US 7,674,867 B2
(45) Date of Patent: *Mar. 9, 2010

(54) PROCESS FOR THE PREPARATION OF AN METAL-ORGANIC COMPOUND COMPRISING AT LEAST ONE IMINE LIGAND

(75) Inventors: Edwin Ijpeij, Sittard (NL); Henricus Arts, Munstergeleen (NL); Gerardus van Doremaele, Sittard (NL); Felix Beijer, Sittard (NL); Francis Van der Burgt, Herten (NL); Martin Alexander Zuideveld, Maastricht (NL)

(73) Assignee: DSM IP Assets B.V., Heerlen (NL)

( * ) Notice: Subject to any disclaimer, the term of this patent is extended or adjusted under 35 U.S.C. 154(b) by 369 days.

This patent is subject to a terminal disclaimer.

(21) Appl. No.: 10/566,839

(22) PCT Filed: Aug. 3, 2004

(86) PCT No.: PCT/EP2004/008707

§ 371 (c)(1),
(2), (4) Date: Feb. 7, 2007

(87) PCT Pub. No.: WO2005/014663

PCT Pub. Date: Feb. 17, 2005

(65) Prior Publication Data

US 2008/0027195 A1    Jan. 31, 2008

(30) Foreign Application Priority Data

Aug. 4, 2003   (EP)   .................. 03077434

(51) Int. Cl.
*C08F 4/642*   (2006.01)
*C08F 4/6592*  (2006.01)

(52) U.S. Cl. .............. 526/161; 526/160; 526/165; 502/103; 502/104; 502/155; 556/13; 556/21; 556/53

(58) Field of Classification Search ............. 556/13, 556/21, 56, 53; 526/161, 165, 160; 502/103, 502/104, 155

See application file for complete search history.

(56) References Cited

U.S. PATENT DOCUMENTS 6,114,481 A    9/2000  McMeeking et al.

FOREIGN PATENT DOCUMENTS

| CA | 2210131 | 1/1999 |
|---|---|---|
| CA | 2243726 | 1/2000 |
| CA | 2243775 | 1/2000 |
| CA | 2243783 | 1/2000 |
| CA | 2261518 | 8/2000 |
| WO | WO 02/070569 | 9/2002 |

OTHER PUBLICATIONS

Mark J. Sarsfield et al; "The reactivity of trimethylsilyliminophosphines towards titanium and zirconium halides"; Journal of the Chemical Society, Dalton Transactions, No. 6; Mar. 21, 2001; pp. 822-827.

*Primary Examiner*—Caixia Lu
(74) *Attorney, Agent, or Firm*—Nixon & Vanderhye, P.C.

(57) ABSTRACT

The invention relates to a process for the preparation of a metal-organic compound, comprising at least one phosphinimine ligand, characterized in that the HA adduct of a phosphinimine ligand according to formula (1) is contacted with a metal-organic reagent of formula (2) in the presence of 1, respectively 2 equivalents of a base, wherein HA represents an acid, of which H represents its proton and A its conjugate base, with Y=N—H as formula (1), and $M^V(L_1)_k(L_2)_l(L_3)_m(L_4)_nX$ as formula (2), and wherein Y is a substituted phosphorous atom, and M represents a group 4 or group 5 metal ion, V represents the valency of the metal ion, being 3, 4 or 5 $L_1$, $L_2$, $L_3$, and $L_4$ represent a ligand or a group 17 halogen atom on M and may be equal or different, k, l, m, n=0, 1, 2, 3, 4 with k+l+m+n+1=V, and X represents a group 17 halogen atom. The invention further relates to a process for the preparation of a polyolefin by making a metal-organic compound according to the process of the invention, wherein the base is an olefin polymerization compatible base, which metal-organic compound is activated anywhere in, or before a polymerization reactor.

16 Claims, No Drawings

PROCESS FOR THE PREPARATION OF AN METAL-ORGANIC COMPOUND COMPRISING AT LEAST ONE IMINE LIGAND

The application is the U.S. national phase of international application PCT/EP2004/008707 filed 3 Aug. 2004 which designated the U.S. and claims benefit Of EP 03077434.3, dated 4 Aug. 2003, the entire content of which is hereby incorporated by reference.

The invention relates to a process for the preparation of an metal-organic compound comprising at least one imine ligand according to formula 1. Metal-organic compounds thus produced are typically used as precatalyst in the production of polyolefins. Imine ligands for these precatalyst can be guanidine, iminoimidazoline, ketimine or phosphinimine, the manufacturing of which is described in WO 02070569, U.S. Pat. Nos. 6,114,481 and 6,063,879 respectively.

The known production processes for phosphinimine comprising metal-organic compounds require at least two steps: (i) the synthesis of a N-trialkylsilyl substituted imine ligand, followed by (ii) contacting this ligand with an metal-organic precursor. However, in the one step process for the manufacturing of the imine ligand, as described in Z. Naturforschung. 29b, 328(1974) (the Staudinger reaction), azide chemistry is required. In this process, the most frequently used azide is azidotrimethylsilane, which is highly toxic and readily hydrolysable, releasing the highly toxic and both temperature and shock sensitive hydrazoic acid. Therefore, mixtures containing (partially) hydrolysed trimethylsilylazide may explosively decompose.

A process for an azide-free preparation of imine ligands (i.e. phosphinimine) is described in Canadian patent application CA 2,261,518. However, this procedure encompasses two reaction steps starting from aminophosphoniumhalides. Another disadvantage of the method described in CA 2,261,518, is the use of harmful and costly reagents, such as n-butyllithium. Finally, in this procedure the imine ligand is substituted with trimethylsilylchloride, which is removed as such in a subsequent reaction of the imine ligand with the metal-organic precursor. Known production processes for guanidine-, ketimine- and iminoimidazoline comprising metal-organic compounds are described in WO 02070569 and U.S. Pat. No. 6,114,481. They are carried out at low temperature and require in some cases a solvent change.

Disadvantage of the known less dangerous method is thus that at least two steps are required, when starting the process with an aminophosphoniumhalide. Purpose of the present invention is to provide a widely applicable method for the manufacturing of a metal-organic compound from an imine and a metal-organic precursor in one step.

This aim is achieved in that an imine ligand according to formula 1, or the HA adduct thereof, wherein HA represents an acid, of which H represents its proton and A its conjugate base, is contacted with a metal-organic reagent of formula 2 in the presence of 1, respectively 2 equivalents of base, wherein

Y=N—R        (formula 1)

wherein Y is selected from a substituted carbon, nitrogen or phosphorous atom and R represents a proton, a protic or an aprotic substituent, and:

$M^v(L_1)_k(L_2)_l(L_3)_m(L_4)_n X$        (formula 2)

wherein:

M represents a group 4 or group 5 metal ion

V represents the valency of the metal ion, being 3, 4 or 5

$L_1, L_2, L_3$, and $L_4$ represent ligands on M and may be equal or different, at least one of the ligands L is chosen from cyclopentadienyl, $C_1$-$C_{20}$ hydrocarbyl (optionally containing hetero- or group 17 halogen atoms), substituted cyclopentadienyls, indenyl, $C_1$-$C_{20}$ hydrocarbyl substituted indenyls, and halogen substituted $C_1$-$C_{20}$ hydrocarbyl substituted indenyls, X represents a group 17 halogen atom k, l, m, n=0, 1, 2, 3, 4 with k+l+m+n+1=V With the method of the invention a metal-organic compound, suitable as precatalyst in olefin polymerisation, is prepared in one step. An additional advantage of the method of the invention is, that during the process hardly any by-products are formed, so that further purification is not necessary (or very limited with respect to state of the art processes). The metal-organic compound prepared by the method of the invention has a higher purity than a metal-organic compound prepared via known production processes and can be used as such in olefin polymerisation processes. An additional advantage of the process of the invention is that the process can be carried out at room temperature, whereas the reaction of the N-trialkylsilyl substituted imine ligand with the metal-organic reagent has to be often carried out at elevated temperatures.

The imine derivative or its HA adduct, as represented in formula 1, is substituted by an Y-and an R group. In the method of the invention, the Y group consists of a substituted carbon, nitrogen or phosphorous atom. If Y represents a substituted carbon atom, the number of substituents is 2. If Y represents a substituted nitrogen atom, the number of substituents is 1 and the number of substituents is 1 or 3 if Y represents a phosphorous atom, depending on the valency of the phosphorous atom. Substituents on carbon, nitrogen or phosphorous may be equal or different, optionally linked with each other, optionally having heteroatoms. Substituents may be protic or aprotic. A protic substituent is defined here as a substituent, which has at least one, group 15 or group 16 atom containing at least one proton.

Examples of protic substituents include $C_1$-$C_{20}$ linear, branched or cyclic hydrocarbyl radicals, substituted with a group 15 or 16 atom bearing at least one hydrogen atom. Preferred protic substituents include phenolic radicals, pyrrolic radicals, indolic radicals, and imidazolic radicals.

The substituent is called aprotic if the substituent lacks a group containing a group 15 or group 16 atom bearing a proton. An unsubstituted aprotic hydrocarbyl radical can be a $C_1$-$C_{20}$ linear, branched or cyclic radical, a hydrogen atom, a halogen atom, a $C_{1-8}$ alkoxy radical, a $C_{6-10}$ aryl or aryloxy radical, an amido radical, or a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula 4, or a germanyl radical of the formula 5.

The substituent R can be H, or being equal as these for the substituent on Y.

Examples of imine ligands according to formula (1) thus include: guanidines, iminoimidazolines, phosphinimines, phenolimines, pyrroleimines, indoleimines and imidazoleimines.

R may be linked with Y, thus forming a ring system, optionally comprising heteroatoms, or optionally comprising functional groups. Examples of ligands comprising such ring systems include: 8-hydroxyquinoline, 8-aminoquinoline, 8-phosphinoquinoline, 8-thioquinoline, 8-hydroxyquinaldine, 8-aminoquinaldine, 8-phosphinoquinaldine, 8-thioquinaldine and 7-azaindole or indazole.

In a preferred embodiment of the method of the invention, R represents a hydrogen atom and Y is selected from the group consisting of:

i) a phosphorus substituent according to the formula:

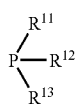

(formula 3)

wherein each $R^{1j}$, with j=1-3 is independently selected from the group consisting of a hydrogen atom, a halogen atom, a $C_{1-8}$ alkoxy radical, a $C_{6-10}$ aryl or aryloxy radical, an amido radical, or a $C_{1-20}$ hydrocarbyl radical unsubstituted or substituted by a halogen atom, a $C_{1-8}$ alkoxy radical, a $C_{6-10}$ aryl or aryloxy radical, an amido radical, a silyl radical of the formula:

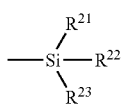

(formula 4)

or a germanyl radical of the formula:

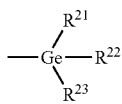

(formula 5)

wherein $R^{2j}$, with j=1-3, is independently selected from the group consisting of hydrogen, a $C_{1-8}$ alkyl or alkoxy radical, $C_{6-10}$ aryl or aryloxy radicals, each substituent $R^{1j}$ or $R^{2j}$ may be linked with another $R^{1j}$ or $R^{2j}$ respectively to form a ring system, ii) a substituent according to formula 6:

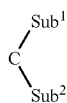

(formula 6)

wherein each of $Sub^1$ and $Sub^2$ is independently selected from the group consisting of hydrocarbyl radicals having from 1 to 30 carbon atoms; silyl radicals, (substituted) amido radicals and (substituted) phosphido radicals, and wherein $Sub^1$ and $Sub^2$ may be linked with each other to form a ring system. Preferably $Sub^1$ and $Sub^2$ are each independently selected from the group of C1-C20 hydrocarbyl radicals, or substituted amido radicals optionally linked by a bridging moiety.

In the process of the invention, HA represents an acid, of which H represents its proton and A its conjugate base. Examples of A are halogenides, such as fluoride, chloride, bromide, or iodide, sulfate, hydrogensulfate, phosphate, hydrogenphosphate, dihydrogenphosphate, carbonate, hydrogencarbonate, aromatic or aliphatic carboxylates, cyanide, tetrafluoroborate, (substituted) tetraphenylborates, fluorinated tetraarylborates, alkyl or aryl sulfonates.

The "number of equivalents of a base" is understood to be the amount of equivalents with respect to the number of imine ligands, or functionalities in the event that one ligand comprises more than one imine functionality. With "1, respectively 2 equivalents of a base", and later on in the application "3, respectively 4 equivalents of a base", is meant that 1, respectively 3 equivalents of a base are required when the imine ligand as such is used, but that 2, respectively 4 equivalents are required, in case the HA adduct of the imine ligand is used.

The metal-organic reagent used in the method of the invention is a reagent according to formula 2. In this formula $L_1$ to $L_4$ can independently be a monoanionic ligand or a group 17 halogen atom.

Examples of monoanionic ligands are: halides like a fluoride, chloride, bromide or iodide, (un)substituted aliphatic or aromatic hydrocarbyls, like $C_1$-$C_{20}$ hydrocarbyl radicals, aryloxy or alkyloxy, cyclopentadienyls, indenyls, tetrahydroindenyls, fluorenyls, tetrahydrofluorenyls, and octahydrofluorenyls, amides, phosphides, sulfides, ketimides, guanidines, iminoimidazolines, phosphinimides, substituted imines, like (hetero)aryloxyimines, pyrroleimines, indoleimines, imidazoleimines or (hetero)aryloxides.

Preferred monoanionic ligands include: fluoride, chloride, bromide, iodide, $C_1$-$C_{20}$ hydrocarbyl radicals, cyclopentadienyl, $C_1$-$C_{20}$ hydrocarbyl substituted cyclopentadienyls, halogen substituted $C_1$-$C_{20}$ hydrocarbyl substituted cyclopentadienyls, indenyl, $C_1$-$C_{20}$ hydrocarbyl substituted indenyls, halogen substituted $C_1$-$C_{20}$ hydrocarbyl substituted indenyls, fluorenyls, $C_1$-$C_{20}$ hydrocarbyl substituted fluorenyls, halogen substituted $C_1$-$C_{20}$ hydrocarbyl substituted fluorenyls, $C_1$-$C_{45}$ substituted phosphinimides, $C_1$-$C_{20}$ substituted ketimides, $C_1$-$C_{30}$ substituted guanidines, $C_1$-$C_{30}$ iminoimidazolines.

Most preferably monoanionic ligands are selected from fluoride, chloride, bromide, iodide, cyclopentadienyl, $C_1$-$C_{20}$ hydrocarbyl (optionally containing hetero- or group 17 halogen atoms), substituted cyclopentadienyls, indenyl, $C_1$-$C_{20}$ hydrocarbyl substituted indenyls, and halogen substituted $C_1$-$C_{20}$ hydrocarbyl substituted indenyls.

Depending on the valency of the metal of the metal-organic reagent, preferably at least one $L_1$, $L_2$, $L_3$, or $L_4$ represents a group 17 atom. If the valency of the metal V=3, one or two ligands L may represent a group 17 atom. If V=4, two or three ligands L may represent a group 17 atom. If V=5, two to four ligands L may represent a group 17 atom. Preferred group 17 atom ligands are fluoride, chloride, bromide or iodide atoms. The most preferred group 17 atom ligand is chloride. At least one of the ligands L is chosen from cyclopentadienyl, $C_1$-$C_{20}$ hydrocarbyl (optionally containing hetero- or group 17 halogen atoms), substituted cyclopentadienyls, indenyl, $C_1$-$C_{20}$ hydrocarbyl substituted indenyls, and halogen substituted $C_1$-$C_{20}$ hydrocarbyl substituted indenyls. $C_1$-$C_{20}$ hydrocarbyl (optionally containing hetero- or group 17 halogen atoms) also includes aryloxy or alkyloxy, octahydrofluorenyls, amides, phosphides, sulfides, ketimides, guanidines, iminoimidazolines, phosphinimides, substituted imines, like (hetero)aryloxyimines, pyrroleimines, indoleimines, imidazoleimines and (hetero)aryloxides.

In the method of the invention an imine ligand or the HA adduct thereof according to formula 1, is contacted with a metal-organic reagent of formula 2 in the presence of 1, respectively 2, equivalents of a base. Examples of a base include, carboxylates (for example potassium acetate), fluorides, hydroxides, cyanides, amides and carbonates of Li, Na, K, Rb, Cs, ammonium and the group 2 metals Mg, Ca, & Ba, the alkali metal (Li, Na, K, Rb, Cs) phosphates and the phosphate esters (eg. $C_6H_5$ OP(O)(ONa)$_2$ and related aryl and alkyl compounds) and their alkoxides and phenoxides, thallium hydroxide, alkylammonium hydroxides and fluorides. Some of these bases may be used in conjunction with a phase transfer reagent, such as for example tetraalkylammonium-, tetraalkylphosphonium salts or crown ethers. Also stronger bases may be applied, like carbanions such as hydrocarbanions of group 1, group 2, group 12 or group 13 elements. Also the metallic alkalimetals of group 1 may be applied as a base.

Preferred bases include amines, phosphanes, organolithium compounds, or organomagnesium compounds, alkali metals, group 1 hydrides or group 2 hydrides More preferred bases are mono-, di-, or tri-, alkylamines or aromatic amines, organolithium compounds, organomagnesium compound, sodium hydride or calciumhydride. Under aromatic amines is understood in this application compounds having a nitrogen atom in an aromatic ring system or mono-, di-, or triarylamines.

Even more preferred bases are triethylamine, pyridine, tripropylamine, tributylamine, 1,4-diaza-bicyclo[2.2.2]octane, pyrrolidine or piperidine organolithium compounds, or organomagnesium compounds. Examples of organomagnesium compounds are: methylmagnesiumhalides, phenylmagnesiumhalides, benzylmagnesiumhalides, biphenylmagnesiumhalides, naphtylmagnesiumhalides, tolylmagnesiumhalides, xylylmagnesiumhalides, mesitylmagnesiumhalides, dimethylresorcinolmagnesiumhalides, N,N-dimethylanilinemagnesiumhalides, dimethylmagnesium, diphenylmagnesium, dibenzylmagnesium, bis(biphenyl)magnesium, dinaphtylmagnesium, ditolylmagnesium, dixylylmagnesium, dimesitylmagnesium, bis(dimethylresorcinol)magnesium, bis(N,N-dimethylaniline)magnesium.

Examples of organolithium compounds are: methyllithium, phenyllithium, benzyllithium, biphenyllithium, naphtyllithium, dimethylresorcinollithium, N,N-dimethylanilinelithium.

In order to make a polyolefin by a borane or borate activatable metal-organic compound, the halide groups of the metal-organic compound from the process of the invention have to be alkylated or arylated in an additional reaction step. This can be done for example with an organolithium compound or an organo magnesium compound. Surprisingly it has been found that such alkylated or arylated metal-organic compound can also be prepared in one step by the process of the invention by carrying out the process in the presence of 3, respectively 4 equivalents of an organomagnesium compound or an organolithium compound as a base. This holds for a metal-organic reagent comprising 3 halogen ligands reacting with 1 imine functionality only. One skilled in the art will understand that metal-organic reagents with 4 or 5 halogen ligands will require 4 respectively 5 equivalents of a base in stead of 3; or 5 respectively 6 equivalents in stead of 4.

The process of the invention is preferably carried out in a solvent. Suitable solvents are solvents that do not react with the metal-organic reagent or the metal-organic compound formed in the process of the invention. Examples of suitable solvents include aromatic and aliphatic hydrocarbons, halogenated hydrocarbons, amides of the aliphatic carboxylic acids and primairy, or secondary amines, DMSO, nitromethane, acetone, acetonitrile, benzonitrile, ethers, polyethers, cyclic ethers, lower aromatic and aliphatic ethers, esters, pyridine, alkylpyridines, cyclic and primary, secondary or tertiary amines, and mixtures thereof. Preferred solvents include aromatic or aliphatic hydrocarbons or mixtures thereof.

The process of the invention can be carried out, by adding respectively 1, respectively 2 equivalents of a base to a mixture of the imine ligand or its HA adduct and the metal-organic reagent thus forming a reaction mixture. The desired metal-organic compound is often formed instantaneously. Surprisingly it turned out that the reaction even with only one equivalent of an organic base appeared to be instantaneously at room temperature to quantitative conversion in the case that an imine is used and 2 equivalents in the case that its HA adduct is used. Another advantage of a process of the invention in the presence of only one equivalent of a base is that the resulting compound may have a higher activity. Without being bound to an explanation, this may be a consequence of the fact that the formation of a coordination complex of the organic base with the metal-organic compound is prevented.

During the reaction, a salt is formed. The reaction mixture as obtained by contacting an imine or its HA adduct may be used as precatalyst in a polyolefin polymerisation without an additional filtration step if the salt formed during the reaction is compatible with the polymerisation process. If a salt free metal-organic compound is required, the salt can be removed by using a filtration. Depending on the solubility of the metal-organic compound, the mixture may be heated and then filtered. An advantage of the present invention is that the filtrate may be used as such without further purification in a following process, such as an alkylation or arylation step or the polymerisation process. If desired, the metal-organic compound may be isolated by distillation of the solvent, by precipitation or by crystallisation from a suitable solvent.

The invention further relates to a process for the preparation of a polyolefin as described in claim 12. Such an olefin polymerisation can be carried out in solution, slurry or in the gas phase.

In a preferred embodiment of the olefin polymerisation the (alkylated) metal-organic compound is formed in situ. By in situ preparation is meant in this context, that the metal-organic compound is made and subsequently activated in or anywhere before the reactor of the polymerisation equipment by contacting an imine or its HA adduct with an metal-organic reagent in the presence of an olefin polymerisation compatible base. In the in situ preparation of the metal-organic compound, it turned out to be favourable to use a surplus of ligand. The number of ligands which are effectively bound to the metal ion are then determined by the number of equivalents of the base. In this case the "number of equivalents of a base" should then be read as the number of equivalents of a base with respect to the equivalents of the ligands being bound to the metal ion. Examples of bases compatible with the olefin polymerisation process include amines, organomagnesium compound, organolithium reagents, organozinc reagents, organoaluminum reagents. More preferred bases are: aromatic amines, organomagnesium compound, organolithium reagents, organozinc reagents, organoaluminum reagents. Most preferred bases are N,N-dimethylaniline, diphenylmethylamine, triphenylamine, dibutylmagnesium, n-butyllithium, $C_1$-$C_{20}$ dihydrocarbylzinc derivatives, diIsobutylaluminium hydride, $C_1$-$C_{20}$ trihydrocarbyl aluminiums, or aluminoxanes. In the case where aluminoxanes are applied as a base, the base can be the activator.

In the olefin polymerisation according to the invention, R preferably represents a hydrogen atom and Y is preferably selected from the group consisting of:

i) a phosphorus substituent according to formula 3 of claim 2 or, ii) a substituent according to formula 6 of claim 2.

Advantages of the process of the invention are: mild conditions, higher yields, higher reaction rates and smaller amounts of by-products. The (alkylated) metal-organic compounds as obtained by the invented process can be used without further purification in the olefin polymerisation resulting in more active catalysts.

The invention will be elucidated with some non-limiting examples:

General Part

Experiments were performed under a dry and oxygen-free nitrogen atmosphere using Schlenk-line techniques. $^1$H-NMR, $^{13}$C-NMR-spectra and $^{31}$P-NMR-spectra were measured on a Bruker Avance 300 spectrometer. Diethyl ether and ligroin were distilled from sodium/potassium alloy; THF and toluene from potassium and sodium, respectively, all having benzophenone as indicator. Tri-ethylamine was distilled from calciumhydride before use. Other starting materials were used as obtained.

EXAMPLE I

Synthesis of
1.3-bis(2.6-dimethylphenyl)-iminoimidazoline
cyclopentadienyl titanium dimethyl To a suspension of 1,3-bis(2,6-dimethylphenyl)-iminoimidazoline (5.86 g, 20.0 mmol) and cyclopentadienyltitanium trichloride (4.39 g, 20.0 mmol) in toluene (200 mL) was added triethylamine (2.02 g, 20 mmol) at ambient temperature. After stirring for 1 hour at ambient temperature, the thick yellow-orange suspension was heated to reflux and filtered hot. The yellow residue was extracted with boiling toluene portions of 10 mL 4 times (leaving a grey-white residue). The combined orange filtrates (separating yellow-orange crystals upon cooling) were cooled to 0° C. Methyl magnesium bromide (14 mL of a 3.0 M solution in diethyl ether, 44 mmol) was added in 10 minutes. The orange suspension turned yellow gradually. The mixture was stirred overnight, then evaporated to dryness. The residue was extracted with boiling ligroin (200 mL) and the resulting suspension was filtered hot. Cooling to approx. −20° C. afforded yellow crystals, which were filtered and washed with cold ligroin to give 2.8 g (32% yield) of NMR pure product. From the partially evaporated mother liquor and $2^{nd}$ ligroin extract, a $2^{nd}$ fraction of pure product was obtained (1.0 g, 11%). Total yield of 1,3-bis(2,6-dimethylphenyl)-iminoimidazoline cyclopentadienyl titanium dimethyl was 43%.

EXAMPLE II

Synthesis of
1.3-bis(2.6-dimethylphenyl)-iminoimidazoline
cyclopentadienyl titanium dimethyl using
methylmagnesium bromide as Base To a suspension of 1,3-bis(2,6-dimethylphenyl)-iminoimidazoline (2.93 g, 10.0 mmol) and cyclopentadienyltitanium trichloride (2.19 g, 10.0 mmol) in toluene (100 mL) was added methylmagnesiumbromide (10 mL of a 3.0 M solution in diethyl ether, 30 mmol) at −80° C. during 10 minutes. The mixture was allowed to warm to ambient temperature to give a yellow suspension. THF (30 mL) was added, and the mixture was stirred for 15 hours. The light yellow suspension was evaporated to dryness. The residue was extracted with boiling ligroin (100 mL). The resulting suspension was filtered hot. The cake was extracted further with hot ligroin (Three times with 60 mL until the filtrate became colourless). The combined yellow filtrates were partially evaporated under reduced pressure to 50 mL. Cooling to approx. 4° C. afforded yellow crystals, which were filtered and washed with cold ligroin to give 2.05 g (47% yield) of NMR pure 1,3-bis(2,6-dimethylphenyl)-iminoimidazoline cyclopentadienyl titanium dimethyl.

EXAMPLE III

Synthesis of
1.3-bis(2.6-diisopropylphenyl)-iminoimidazoline
cyclopentadienyl titanium dichloride a. Synthesis of 1,3-bis(2,6-diisopropylphenyl)-iminoimidazoline To a mixture of 2,6-diisopropylaniline (260 g, 1.47 mol) in ethanol (1200 mL) was slowly added glyoxal (108.5 g of a 40 w-% in water solution, 0.75 mol). The solution turned intensely red, then intensely yellow. The mixture was heated to reflux overnight. Cooling to 4 degrees resulted in crystallisation of yellow material, which was filtered and washed with cold ethanol until filtrate became bright yellow (instead of brown). The bright yellow powder was dried (202.6 g, 72%). This diimine (100 g, 0.27 mol) was dissolved in ethanol (1000 mL). The mixture was cooled to 0° C. Sodium borohydride (102.1 g, 2.7 mol) was added in portions during 1 hour. The mixture was allowed to warm to room temperature, then stirred 1 hour. The mixture was heated to reflux gently (gas evolution!) and heated to reflux for 1 hour. After cooling, the mixture was admixed with water (2 L), and the suspension filtered. The yellow precipitate was dried (100.1 g, 98%). 57 g (0.15 mol) of the diamine was dissolved in toluene (250 mL) and heated to reflux. A solution of cyanogen bromide (19.1 g, 0.18 mol) in toluene (100 mL) was added during the course of ~1 hour, resulting in formation of a grey precipitate in an orange-red solution. After stirring at reflux for 1 hour, the mixture was cooled. The precipitate was filtered, washed with toluene and ligroin (to give 47.1 g yellow light powder). This powder was dissolved in water/ethanol 400/500 mL, and 10.0 M NaOH in water was added until strongly basic (pH>10). The precipitate was filtered and washed with water, then dried to give 37.3 g (61.4% yield) of near pure product. The iminoimidazoline can be crystallized to give pure material as colourless crystals from boiling ligroin (270 mL) and filtering hot to remove some insoluble material (recovery 67%).

b. Synthesis of 1,3-bis(2,6-diisopropylphenyl)-iminoimidazoline cyclopentadienyl titanium dichloride To a suspension of 1,3-bis(2,6-diisopropylphenyl)-iminoimidazoline (1.02 g, 2.5 mmol) and cyclopentadienyltitanium trichloride (0.55 g, 2.5 mmol) in toluene (20 mL) was added triethylamine (0.25 g, 2.5 mmol) at ambient temperature. After stirring for 2 hours, the thick yellow-orange suspension was filtered, and the filtrate evaporated to dryness to afford 1.31 g (89% yield) of NMR-pure 1,3-bis(2,6-diisopropylphenyl)-iminoimidazoline cyclopentadienyltitanium dichloride.

c. Synthesis of 1,3-bis(2,6-diisopropylphenyl)-iminoimidazoline cyclopentadienyl titanium dichloride (reversed addition)

The same result as under b. was obtained when cyclopentadienyltitanium trichloride and triethylamine were admixed in toluene, and then ligand was added.

EXAMPLE IV

Synthesis of
1.3-bis(2.6-diisopropylphenyl)-iminoimidazoline
cyclopentadienyl titanium dimethyl To a suspension of 1,3-bis(2,6-diisopropylphenyl)-iminoimidazoline (2.06 g, 5.0 mmol) and cyclopentadienyltitanium trichloride (1.10 g, 5.0 mmol) in toluene (40 mL) was added triethylamine (0.8 mL, 5.7 mmol) at ambient temperature. After stirring for 2 hours, the thick yellow-orange suspension was filtered, and the residue washed with toluene. The clear and orange filtrate was partially evaporated (~10 mL solvent removed). After cooling to −78° C. (dry ice/acetone), methyl magnesium bromide solution (3.3 mL of a 3M solution in diethyl ether, 10.0 mmol) was added. The temperature of the mixture was allowed to rise to ambient temperature and the mixture was stirred overnight. The yellow suspension was evaporated to dryness. The residue was extracted with boiling ligroin (80 mL) and the resulting suspension was filtered hot. Evaporation to ~30 mL and cooling to approx. 4° C. afforded yellow crystals, which were filtered and washed with cold ligroin to give 1.38 g (51% yield) of NMR pure product. From the partially evaporated mother liquor, a $2^{nd}$ fraction of pure 1,3-bis(2,6-diisopropylphenyl)-iminoimidazoline cyclopentadienyl titanium dimethyl was obtained (0.58 g, 19%). Total yield of 1,3-bis(2,6-diisopropylphenyl)-iminoimidazoline cyclopentadienyl titanium dimethyl: 70%.

EXAMPLE V

Synthesis of Bis(1-N-cyclohexylcarboximino-6-t-butylphenoxy)titaniumdichloride

To a solution of titanium(IV)chloride (5 mL, 1.0M in toluene, 5.0 mmol) in toluene (40 mL) was added 1-N-cyclohexylcarboximine-6-t-butylphenol (2.59 g,10.0 mmol) and triethylamine (1.02 g, 10 mmol) subsequently. The reaction mixture was stirred for 16 hours at room temperature. The solid was allowed to precipitate and the supernatant was decanted. The remaining solid was extracted twice with a mixture of toluene/THF (80 mL, 1/1, V/V). The solvents were removed in vacuo resulting in 2.80 g (88%) of a red solid. NMR data were consistent with those reported in EP0874005, but the yield of 88% is substantially higher than the 18% yield reported in EP 0874005.

EXAMPLE VI

Synthesis of Bis(1-N-cyclohexylcarboximino-6-t-butylphenoxy)zirconiumdichloride

To zirconium(IV)chloride (1.40 g, 4.5 mmol) was added THF(40 mL). The mixture was cooled to 0° C. and a solution of 1-N-cyclohexylcarboximine-6-t-butylphenol (2.31 g, 8.9 mmol) in toluene (25 mL) was added. Then, triethylamine (0.89 g, 8.9 mmol) was added and the mixture was stirred for 15 hours at room temperature. The solids were allowed to precipitate and the supernatant was decanted from the solid. The solid was extracted with a mixture of toluene/THF (80 mL, 1/1, V/V). The combined extracts were evaporated to dryness resulting in 2.95 g (97%) of a light yellow powder. NMR data were consistent with those reported in EP0874005, but the yield was significantly higher than the yield of 43% reported in EP 0874005.

Part B Examples Related to the Polymerisation of an Olefinic Copolymer.

Polymerisation Equipment.

The batch copolymerisation was carried out in a polymerisation equipment, having a catalyst dosing vessel equipped with a catalyst dosing pump for the addition of the catalyst to a 2-liter batch autoclave equipped with a double intermig stirrer and baffles. The reactor temperature was controlled by a Lauda Thermostat. The feed streams (solvents and monomers) were purified by contacting them with various absorption media as is known in the art. During polymerisation, the ethylene (C2) and propylene (C3) were continuously fed to the gas cap of the reactor. The pressure of the reactor was kept constant by means of a back-pressure valve.

Copolymerisation Experiments.

In an inert atmosphere of nitrogen, the reactor was filled with pentamethylheptanes (PMH) (950 mL) and an amount of MAO (Crompton 10 wt % in toluene) and 4-methyl-2,6-di-tert-butylphenol (BHT) as given in Tables 1 and 2. The reactor was heated to 90° C., while stirring at 1350 rpm. The reactor then was pressurized to 0.7 MPa and kept under a determined flow of 200 NL/h of ethylene and 400 NL/h of propylene for 15 minutes. Then, the catalyst components were added to the reactor and possible residual material was rinsed with PMH (50 mL) and subsequently fed to the reactor.

When tritylium tetrakis(perfluorophenyl)borate (TBF20) was used, the TBF20 was added directly after the catalyst addition. After 10 minutes of polymerisation, the monomer flow was stopped and the solution was slowly poured into a 2 L Erlenmeyer flask, and dried over night at 100° C. under reduced pressure.

The polymers were analysed by FT-IR to determine the amount of incorporated C3 and Intrinsic Viscosity being an indication for the average molecular weight.

Polymer Analysis.

The amount of incorporated C3 in weight per cents relative to the total composition, was measured by means of Fourier transformation infrared spectroscopy (FT-IR) according to ASTM D 3900 method A.

The Intrinsic Viscosity (IV) was measured at 135° C. in decaline.

EXAMPLES 1-11

In situ Polymerisation

These catalysts were prepared in the polymerisation equipment by adding amounts as depicted in table 1a of toluene solutions of the metal-organic reagent, the ligand and the base successively to the catalyst dosing vessel in toluene (15 mL). After stirring for 5 minutes the mixture was injected into the polymerisation reactor. Results are shown in Table 1b.

The experiments 1, 2, 5, 12 and 13 were carried by adding a prepared and purified metal-organic compound to the catalyst dosing vessel, and subsequently fed to the polymerisation reactor.

It can be concluded from the comparison of all experiments with experiment 2, that all in situ prepared catalysts produce copolymers having a higher molecular weight than the copolymer produced with the $CpTiCl_3$ and the base only, which allows preparation of a polyolefin by just adding a metal-organic reagent, an imine ligand and at least 1 equivalent of a base to the polymerisation equipment.

From Examples 8 and 10 it can be concluded that a process in the presence of between 5 and 10 equivalents of the imine ligand according to formula 1 is mostly preferred.

Polymerisation

For the polymerisation an aliquot (5 mL) of the mixture obtained above, was diluted with toluene (35 mL). From this TABLE 1a In situ polymerisations: polymerisation conditions

| Example | Metal-organic reagent/compound | Metal-organic compound dosage (μmol Ti) | ligand | Ligand dosage (μmol) | Base | Base dosage (μmol) | Activator system | Al/Ti Molar ratio | BF20/Ti Molar ratio | BHT/Al Molar ratio | Pol. Time (min) |
|---|---|---|---|---|---|---|---|---|---|---|---|
| 1 | 1 | 0.5 | — | — | — | — | MAO/BHT | 600 | — | 2 | 10 |
| 2 | CpTiCl3 | 0.75 | — | — | Et3N | 0.75 | MAO/BHT | 3000 | — | 1 | 10 |
| 3 | CpTiCl3 | 1.0 | L1 | 2.0 | Et3N | 1.0 | MAO/BHT | 3000 | — | 1 | 10 |
| 4 | CpTiCl3 | 0.4 | L1 | 0.8 | Et3N | 0.4 | MAO/BHT/TBF20 | 3000 | 2 | 1 | 10 |
| 5 | 2 | 0.05 | — | — | — | — | MAO/BHT | 3000 | — | 1 | 10 |
| 6 | CpTiCl3 | 0.75 | L2 | 1.5 | Et3N | 0.75 | MAO/BHT | 3000 | — | 1 | 10 |
| 7 | CpTiCl3 | 0.75 | L2 | 0.75 | Et3N | 0.75 | MAO/BHT | 3000 | — | 1 | 10 |
| 8 | CpTiCl3 | 0.75 | L2 | 3.75 | Et3N | 0.75 | MAO/BHT | 3000 | — | 1 | 10 |
| 10 | CpTiCl3 | 0.25 | L2 | 2.5 | Et3N | 0.25 | MAO/BHT | 3000 | — | 1 | 10 |
| 11 | CpTiCl3 | 0.4 | L2 | 2 | Et3N | 0.4 | MAO/BHT/TBF20 | 3000 | 2 | 1 | 3 |

Metal-organic compound 1 = tris(N,N-dimethylamido)phosphoraneimido cyclopentadienyl titanium(IV) dichloride
Metal-organic compound 2 = 1,3-bis(2,6-dimethylphenyl)-iminoimidazoline cyclopentadienyl titanium dibenzyl
L1 = N,N,N',N',N'',N''-hexamethylphosphorimidic triamide
L2 = 1,3-bis(2,6-dimethylphenyl)-iminoimidazoline TABLE 1b In situ polymerisations: polymerisation results

| Example | ΔT (° C.) | Yield (g) | residual Ti in polymer (ppm) | Incorporated C3⁻ (wt %) | IV (dl/g) |
|---|---|---|---|---|---|
| 1 | 0.8 | 2.93 | 8.2 | 41 | 2.4 |
| 2 | 0.5 | 2.74 | 13.1 | 62 | 0.96 |
| 3 | 3.5 | 8.97 | 5.3 | 46 | Nd |
| 4 | 1.6 | 5.34 | 3.6 | 42 | Nd |
| 5 | 1.8 | 6.09 | 0.4 | 48 | 2.77 |
| 6 | 2.0 | 8.41 | 4.3 | 54 | 2.07 |
| 7 | 0.8 | 3.76 | 9.5 | | |
| 8 | 4.2 | 14.37 | 2.5 | 51 | 2.32 |
| 10 | 4.9 | 19.84 | 0.6 | 52 | 2.29 |
| 11 | 4.4 | 18.05 | 1.1 | 50 | |

EXAMPLES 17-18

Polymerisation with Unpurified triisopropylphosphoraneimido cyclopentadienyl titanium(IV) dichloride Catalyst Preparation Cyclopentadienyltitaniumtrichloride (86 mg, 0.39 mmol) and triisopropylaminophosphonium bromide (0.10 g, 0.39 mmol) were mixed in toluene (10 mL). Triethylamine (80 mg, 0.8 mmol) was added and the reaction mixture was stirred at room temperature for 2 hours.

diluted mixture, an aliquot (0.03 mL) was added to the catalyst dosing vessel containing PMH (15 mL). This mixture was subsequently added to the polymerisation reactor and the catalyst dosing vessel was rinsed with PMH (50 mL).

EXAMPLES 19-20

Polymerisation with Unpurified 1.3-bis(2.6-dimethylphenyl)-iminoimidazoline cyclopentadienyl titanium dibenzyl Catalyst preparation Cyclopentadienyltitaniumtrichloride (75 mg, 0.34 mmol) and 1,3-bis(2,6-dimethylphenyl)-iminoimidazoline (0.10 g, 0.34 mmol) were mixed in toluene (10 mL). Triethylamine (34 mg, 0.34 mmol) was added and the reaction mixture was stirred at room temperature for 2 hours.

Polymerisation

For the polymerisattion an aliquot (0.75 mL) of the mixture obtained above was diluted with toluene (25 mL). From this diluted mixture, an aliquot (0.15 mL) was added to the catalyst dosing vessel containing PMH (15 mL). This mixture was subsequently added to the polymerisation reactor and the catalyst dosing vessel was rinsed with PMH (50 mL). Examples 17-20 indicate that polymerisation of olefinic monomers is possible by just adding a mixture of a metal-organic reagent, an imine ligand and at least one equivalent of a base to a polymerisation reactor with olefinic monomers, without the need to firstly purify (i.c filtrate) a catalyst (i.c. metal-organic compound) from the mixture.

TABLE 2a

Polymerisation with unpurified catalysts: polymerisation conditions

| Example | Metal-organic compound | Metal-organic compound dosage (μmol Ti) | Activator system | Al/Ti Molar ratio | BF20/Ti Molar ratio | BHT/Al Molar ratio | Pol. Time (min) |
|---|---|---|---|---|---|---|---|
| 17 | 4 | 0.15 | MAO/BHT | 3000 | — | 2 | 10 |
| 18 | 4 | 0.15 | MAO/BHT/TBF20 | 3000 | 2 | 2 | 10 |
| 19 | 5 | 0.15 | MAO/BHT | 3000 | — | 1 | 10 |
| 20 | 5 | 0.15 | MAO/BHT | 3000 | — | 1 | 10 |
| 21 | 6 | 0.15 | MAO/BHT | 300 | — | 2 | 10 |

Metal-organic compound 4 = triisopropylphosphoraneimido cyclopentadienyl titanium(IV) dichloride
Metal-organic compound 5 = 1,3-bis(2,6-dimethylphenyl)-iminoimidazoline cyclopentadienyl titanium dichloride
Metal-organic compound 6 = triisopropylphosphoraneimido cyclopentadienyl titanium(IV) dimethyl TABLE 2b Polymerisation with unpurified catalysts: polymerisation results

| Example | ΔT (° C.) | Yield (g) | residual Ti in polymer (ppm) | Incorporated C3⁻ (wt %) | IV (dl/g) |
|---|---|---|---|---|---|
| 17 | 2.0 | 6.55 | 1.1 | 43 | Nd |
| 18 | 2.7 | 8.11 | 0.9 | 40 | Nd |
| 19 | 4.8 | 18.75 | 0.4 | 501 | 2.33 |
| 20 | 4.2 | 16.5 | 0.4 | 53 | nd |
| 21 | 3.0 | 8.82 | 0.8 | 43 | nd |

The invention claimed is:

1. A one step process for the preparation of a metal-organic compound, wherein at least one imine ligand compound according to formula 1 or the HA adduct thereof, wherein HA represents an acid, of which H represents its proton and A its conjugate base, is contacted with a metal-organic regent of formula 2 in the presence of 1 or 2 equivalents of a base respectively, with

  as formula 1, wherein Y is selected from a substituted carbon, nitrogen, or phosphorous atom and R represents a substituent, and with

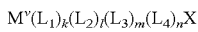  as formula 2, wherein: M represents a group 4 or group 5 metal ion
V represents the valency of the metal ion, being 3, 4 or 5
L1, L2, L3, and L4 represent a ligand or a group 17 halogen atom on M and may be equal or different, at least one of the ligands L is chosen from cyclopentadienyl, C1-C20 hydrocarbyl, substituted cyclopentadienyls, indenyl, C1-C20 hydrocarbyl substituted indenyls, and halogen substituted C1-C20 hydrocarbyl substituted indenyls
X represents a group 17-halogen atom,
k, l, m, n=0, 1, 2, 3, 4 with k+l+m+n+1=V.

2. A process according to claim 1 wherein R represents a hydrogen atom and wherein Y is selected from the group consisting of i) a phosphorus substituent defined by the formula:

  (formula 3)

wherein each R1j, with j =1-3 is independently selected from the group consisting of a hydrogen atom, a halogen atom, a C1-8 alkoxy radical, a C6-10 aryl or aryloxy radical, an amido radical, a C1-20 hydrocarbyl radical unsubstituted or substituted by a halogen atom, a C1-8 alkoxy radical, a C6-10 aryl or aryloxy radical, an amido radical, a silyl radical of the formula:

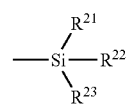  (formula 4)

and a germanyl radical of the formula:

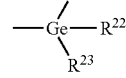  (formula 5)

wherein R2j is independently selected from the group consisting of hydrogen, a C1-8 alkyl , a alkoxy radical, a C6-10 aryl and aryloxy radicals,
each substituent R1j or R2j may be linked with another R1 or R2 to form a ring system,
ii) a substituent defined by formula 6:

  (formula 6)

wherein each of Sub1 and Sub2 is independently selected from the group consisting of hydrocarbyl radicals having from 1 to 30 carbon atoms; silyl radicals, amido radicals, substituted amido radicals, phosphido radicals, and substituted phosphido radicals; and wherein Sub1 and Sub2 may be linked with each other to form a ring system.

3. A process according to claim 1, wherein the base is a dialkylamine, a trialkylamine, a monoarylamine, diarylamine or a triarylamine.

4. A process according to claim 1, wherein the base is triethylamine, pyridine, tripropylamine, tributylamine, 1,4-diaza-bicyclo [2.2. 2]octane, pyrrolidine or piperidine.

5. A process according to claim 1, wherein the base is a carboxylate, a fluoride, a hydroxide, a cyanide, an amide, a carbonate of Li, Na, K, Rb, Cs, or an ammonium salt or a group 2 metal salt of Mg, Ca, or Ba thereof, an alkali metal phosphate, or phosphate ester, or their alkoxides or phenoxides, thallium hydroxide, alkylammonium hydroxides or fluorides, or alkali metals, hydrides or carbonates of Li, Na, K, Rb, Cs or group 2 hydrides.

6. A process according to claim 5, wherein the alkali metal is chosen from Li, Na, or K.

7. A process according to claim 1, wherein the base is a group 1, 2, 12, 13 hydrocarbanion.

8. A process according to claim 7, wherein the base is an organomagnesium- or an organolithium compound.

9. A process according to claim 1 wherein the reaction is carried out in an aprotic solvent.

10. A process according to claim 9, wherein the solvent is the base.

11. Process for the preparation of a polyolefin by making a metal-organic compound according to the process of claim 1, wherein the base is an olefin polymerisation compatible base, which metal-organic compound is activated anywhere in, or before a polymerisation reactor.

12. Process according to any of claims 11, wherein the metal-organic compound is formed used without purification.

13. Process according to claim 11, wherein the metal-organic compound is formed in the polymerisation equipment.

14. Process according to claim 13, wherein said process is performed in the presence of between 5 and 10 equivalents of the imine ligand compound according to formula 1.

15. A process according to claim 1, wherein said C1-C20 hydrocarbyl contains hetero- or group 17 halogen atoms.

16. A process according to claim 5, wherein said an alkali metal phosphate is selected from the group consisting of Li, Na, K, Rb, and Cs.

* * * * *